(12) United States Patent
Lai et al.

(10) Patent No.: US 10,551,340 B2
(45) Date of Patent: Feb. 4, 2020

(54) CAPACITOR-BASED FLUID SENSING UNITS AND OPERATING METHODS THEREOF

(71) Applicant: CHANG GUNG UNIVERSITY, Taoyuan (TW)

(72) Inventors: Chao-Sung Lai, Taoyuan (TW); Chia-Ming Yang, Taoyuan (TW); Hsin-Yin Peng, Taipei (TW); Wei-Yin Zeng, Taoyuan (TW); Chun-Hui Chen, Nantou County (TW)

(73) Assignee: CHANG GUNG UNIVERSITY, Taoyuan (TW)

( * ) Notice: Subject to any disclaimer, the term of this patent is extended or adjusted under 35 U.S.C. 154(b) by 4 days.

(21) Appl. No.: 15/406,644

(22) Filed: Jan. 13, 2017

(65) Prior Publication Data
US 2018/0074002 A1    Mar. 15, 2018

(30) Foreign Application Priority Data
Sep. 9, 2016   (TW) .............................. 105129316 A (51) Int. Cl.
*G01N 27/22* (2006.01)
(52) U.S. Cl.
CPC ................................. *G01N 27/223* (2013.01)

(58) Field of Classification Search
CPC .................................................. G01N 27/223
See application file for complete search history.

(56) References Cited

U.S. PATENT DOCUMENTS

| | | | |
|---|---|---|---|
| 7,193,290 B2* | 3/2007 | Benzel ................. | G01N 27/121 257/414 |
| 2004/0149032 A1* | 8/2004 | Sell ........................ | G01F 23/263 73/304 C |
| 2007/0113642 A1* | 5/2007 | Bonne ................... | G01F 1/6845 73/204.11 |
| 2013/0228475 A1* | 9/2013 | Setford .............. | G01N 27/3272 205/782 |

* cited by examiner

*Primary Examiner* — Patrick Assouad
*Assistant Examiner* — Feba Pothen
(74) *Attorney, Agent, or Firm* — Cheng-Ju Chiang (57) ABSTRACT

The present invention provides capacitor-based fluid sensing units. The capacitor-based fluid sensing unit comprises a substrate, a first electrode configured on the substrate, a sensing layer configured on the first electrode, a second electrode configured on the sensing layer. More particularly, the second electrode is a porous electrode, while the sensing layer is made of a porous dielectric material and has a thickness between 50 nm and 5 mm. Permittivity of the sensing layer changes as fluid permeates from the second electrode to the sensing layer. The subsequent change in capacitance of the capacitor-based fluid sensing unit is used to determine the volume of the fluid.

8 Claims, 6 Drawing Sheets

CAPACITOR-BASED FLUID SENSING UNITS AND OPERATING METHODS THEREOF

CROSS-REFERENCE TO RELATED APPLICATION AND CLAIM OF PRIORITY

This application claims the benefit of Taiwanese Patent Application No. 105129316, filed on Sep. 9, 2016, in the Taiwan Intellectual Property Office, the disclosure of which is incorporated herein in its entirety by reference.

1. TECHNICAL FIELD

At least one embodiment of the prevent invention relates to capacitor-based fluid sensing units and the operating methods thereof. More particularly, capacitor-based fluid sensing units having porous electrodes and porous dielectric materials, as well as operating methods having a step of applying bias voltage to generate heat to dry the sensing layer.

2. DESCRIPTION OF THE RELATED ART

Hydrometers are widely used in manufacturing, high-tech, and medical industries and also are important tool in everyday life. Wet/dry bulbs thermometers and hair hygrometers are soon not enough for the sophisticated needs nowadays. Unlike thermometers, sensitivity and response speed of hygrometers are easily affected by external factors including air pressure and temperature.

Known fluid sensing units in the art are classified into either resistance-based or capacitor-based fluid sensing unit. The resistance-based fluid sensing units usually comprises a fluid sensing film covered on a substrate, where the fluid sensing film can absorb moisture in air. The changes in resistance and resistivity of the fluid sensing film, induced by moisture absorption, are used to determine humidity. The resistance-based fluid sensing units provide sensitive results but have poor linearity and are not interchangeable. The capacitor-based fluid sensing units usually comprise a macromolecule thin-film capacitor made of polystyrene, polyimide, or cellulose acetate. Similarly, environmental humidity and permittivity and capacitance of the macromolecule thin-film capacitor and are positive correlated. The capacitor-based fluid sensing units provide fast response and sensitive results.

Dielectric materials commonly found in the art are calcium oxide (CaO), calcium chloride ($CaCl_2$), sodium silicate ($Na_2O_3Si$), and silica ($SiO_2$). However, calcium oxide is known for its toxicity after absorbing water and being converted into calcium hydroxide. Calcium chloride solution, on the other hand, constitutes part of water pollution as its alkaline property. Sodium silicate and silica require heat treatment to reuse. Moreover, the sensitivity of known fluid sensing units is largely affected by external factors; these fluid sensing units are accordingly only used to detect organic components in solution.

SUMMARY

At least one embodiment of the present invention provides to a capacitor-based fluid sensing unit having a porous and inorganic dielectric material to mitigate disadvantages in conventional dielectric materials. The conventional dielectric materials are mostly organic and toxic in water, and therefore can only be used to detect organic materials. The sensitivity of conventional dielectric materials is easily affected by humidity and thus requires additional treatments before reuse. In contrast, the porous dielectric material in the present embodiment is toxin-free, environmental friendly and heat-stable. The dielectric material can depose formaldehyde and total volatile organic compound (TOVC), as well as absorb water and regulate humidity. The porous dielectric material therefore provides high stability and fast response, and is suitable for being used in wearable devices to detect perspiration volume by sensing the permittivity and diffusion area of perspiration. Moreover, the present embodiment utilizes bias voltage to generate heat to evaporate the perspiration in the sensing layer before reuse.

Some embodiments of the present invention provide a capacitor-based fluid sensing unit. The capacitor-based fluid sensing unit comprises a substrate; a first electrode, disposed on the substrate; a sensing layer, disposed on the first electrode, wherein the sensing layer is made of a porous dielectric material, and wherein the sensing layer has a thickness between 50 nm and 5 mm; and a second electrode, disposed on the sensing layer, wherein the second electrode is a porous electrode.

In the previous embodiments, the first electrode and the second electrode each is made of one selected from the group consisting of gold (Au), silver (Ag), indium tin oxide (ITO), and the combination thereof. In some preferred embodiments, the first electrode and the second electrode are made of gold. The porous dielectric material comprises silicon dioxide (SiO2). In some preferred embodiments, the porous dielectric material is diatomaceous earth, spin-on glass (SOG), or mesoporous silica (e.g., MCM-41 and SBA-15). The porous electrode is an interdigitated electrode, a comb-shaped electrode, or a mesh electrode. The substrate is made of one selected from the group consisting of silicon wafer, glass, plastic, and the combination thereof. In some preferred embodiments, the substrate is made of polyethylene terephthalate (PET).

Perspiration excreted from pores on the skin can permeate to the sensing layer through the second electrode which is porous. The perspiration in the sensing layer changes the permittivity of the sensing layer and therefore changes the capacitance value of the capacitor-based fluid sensing unit. Converting from the permittivity and the diffusion area, the perspiration volume can be determined. Accordingly, the present invention can be implemented in wearable devices in some embodiments. In the present embodiments, the sensing layer made of porous and inorganic dielectric materials (e.g., silicon dioxide and porous silicon materials) is toxin-free and environmental friendly. This dielectric material can depose formaldehyde and total volatile organic compound (TOVC), as well as regulate humidity. The capacitor-based fluid sensing unit in the present embodiments uses improved structure and materials, therefore can absorb solution, allow the permeation of the solution, and provide fast response and high stability.

Some embodiments of the present invention provide an operating method of capacitor-based fluid sensing units. The operating method comprises a step of providing a capacitor-based fluid sensing unit as disclosed in the aforementioned embodiments of the present invention; a step of providing a solution to the second electrode; a step of applying a first bias voltage to the capacitor-based fluid sensing unit; a step of detecting a capacitance value of the capacitor-based fluid sensing unit; determining a volume of the solution based on the capacitance value; and a step of applying a second bias voltage to the capacitor-based fluid sensing unit to dry the sensing layer. In some preferred embodiments, the step of applying the first bias voltage is performed 2 to 5 minutes after the step of providing the solution to the second electrode. In some other preferred embodiments, the first bias voltage and the second bias voltage each is between 0.05 V and 0.1 V. In yet some other preferred embodiments, the solution is water or perspiration.

In the step of applying a second bias voltage to the capacitor-based fluid sensing unit, heat generated by the second bias is used to evaporate the solution in the sensing layer. The capacitor-based fluid sensing unit can therefore be reused after evaporation of the solution.

DESCRIPTION OF THE PREFERRED EMBODIMENTS

At least one embodiment of the prevent invention is a capacitor-based fluid sensing unit and the operating method thereof.

Figure 1:
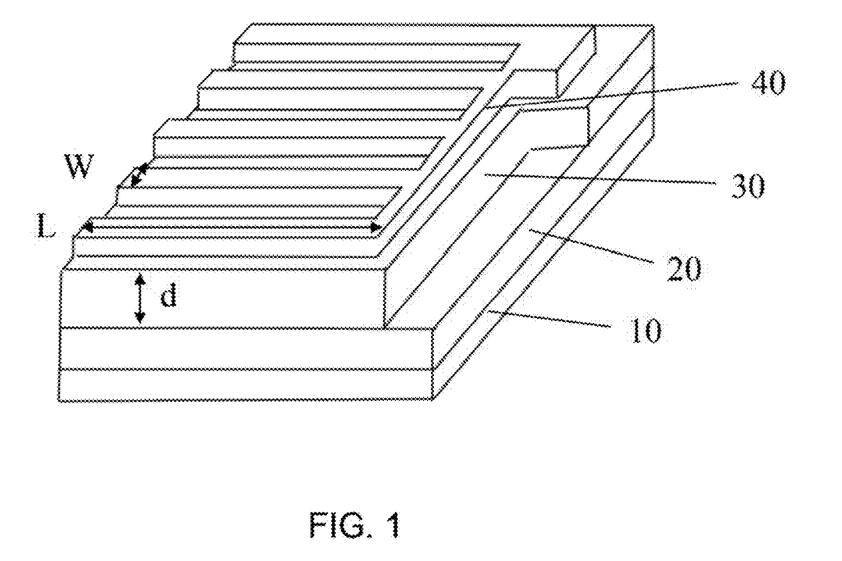
FIG. 1 is a schematic diagram illustrating a capacitor-based fluid sensing unit, in accordance with some embodiments of the present invention.

FIG. 1 is a schematic diagram illustrating a capacitor-based fluid sensing unit, in accordance with some embodiments of the present invention. The capacitor-based fluid sensing unit 1 comprises, from bottom to top, a substrate 10, a first electrode 20 disposed on the substrate 10, a sensing layer 30 disposed on the first electrode 20, and a second electrode 40, disposed on the sensing layer 30. In accordance with some embodiments of the present invention, the method of manufacturing the capacitor-based fluid sensing unit 1 comprises a step of vapor depositing chromium/gold (Cr/Au) on a polyethylene terephthalate (PET) substrate to form the first electrode 20, a step of applying adhesive on the first electrode 20 with a dropper, a step of drying the adhesive under 65° C. with a magnetic hotplate stirrer, a step of applying a mixture of water and a porous dielectric material (i.e., diatomaceous earth in the present embodiments) on the adhesive, a step of drying the mixture under 65° C. with the magnetic hotplate stirrer to form the sensing layer 30, a step of vapor depositing Cr/Au on the sensing layer 30 with a metal mask to form the second electrode 40. More particularly, the thickness of the sensing layer 30 is between 50 nm and 5 mm, and the second electrode 40 is a porous and comb-shaped electrode. In some preferred embodiments, the first electrode 20 is covered by the sensing layer 30 and thus is isolated from oxygen in the air and the oxidation of the first electrode 20 can be mitigated.

Aside from PET, the substrate 10 may be made of one selected from the group consisting of silicon wafer, glass, plastic, and the combination thereof in some other embodiments. Aside from Cr/Au, the first electrode 20 and the second electrode 40 each may be made of one selected from the group consisting of gold (Au), silver (Ag), indium tin oxide (ITO), and the combination thereof in some other embodiments. Aside from diatomaceous earth, the porous dielectric material may be spin-on glass (SOG), mesoporous silica (e.g., MCM-41 and SBA-15), or other porous dielectric materials comprising silicon in some other embodiments. Aside from the comb-shaped electrode, the porous electrode may be an interdigitated electrode or a comb-shaped electrode in some other embodiments.

Figure 2:
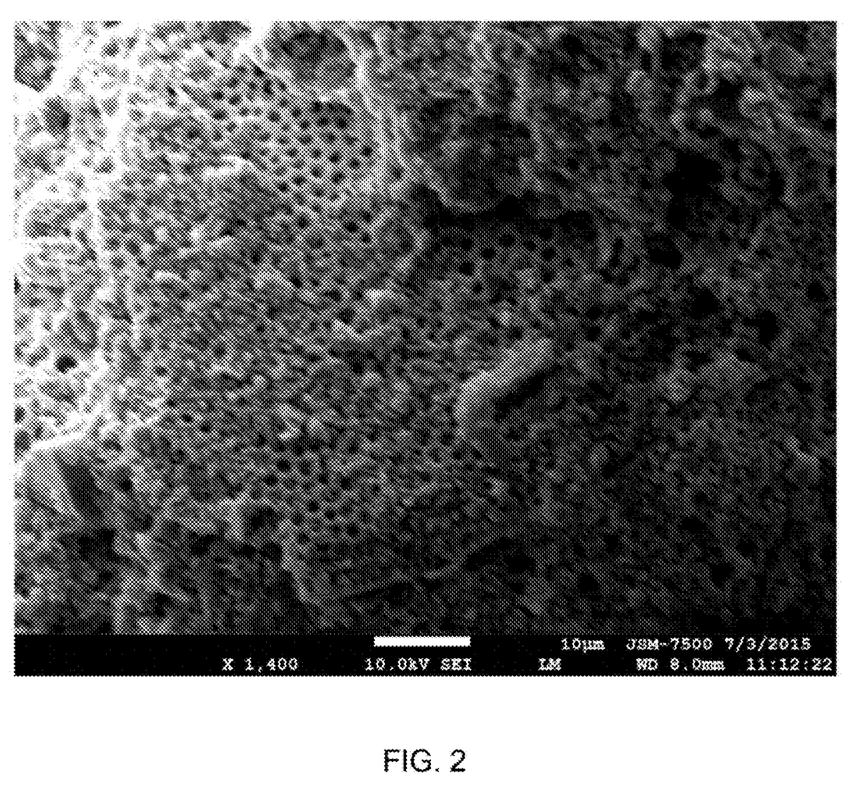
FIG. 2 is an SEM image (1400×) of a sensing layer made of diatomaceous earth, in accordance with some embodiments of the present invention.
Figure 3:
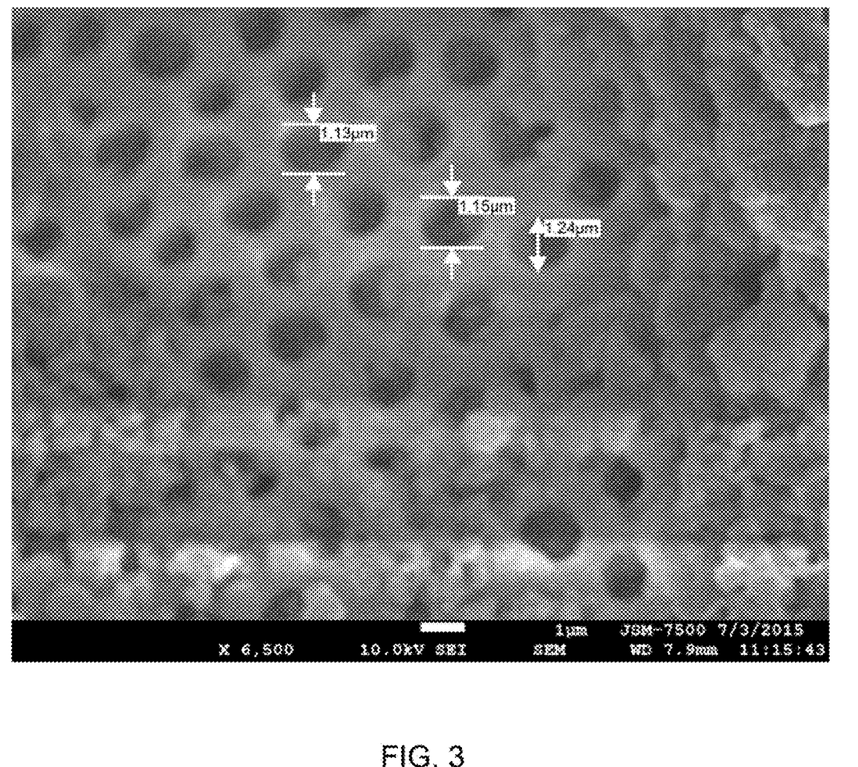
FIG. 3 is an SEM image (6500×) of a sensing layer made of diatomaceous earth, in accordance with some embodiments of the present invention.

FIGS. 2-3 are scanning electron microscope (SEM) images of a sensing layer made of diatomaceous earth, in accordance with some embodiments of the present invention. The resolutions of FIGS. 2-3 are 4 μm and 1 μm respectively. In the SEM images, the diatom remains form multiple holes. In additions to the holes, the surface of diatom remains contains multiple pores in a random and irregular arrangement. The diameters of pores are about 1.13 μm, 1.14 μm, 1.24 μm. The combination of larger holes and smaller pores elevates porosity of diatomaceous earth and provides good permeability and strong water absorption to the diatomaceous earth. Diatomaceous earth is natural, environmental friendly, toxin-free, and heat-stable. Diatomaceous earth also has the ability to depose formaldehyde and total volatile organic compound (TOVC) and shows a superior efficiency to regulate humidity as compared to binchoutan. Aside from diatomaceous earth, the porous dielectric material may be SOG or mesoporous silica (e.g., MCM-41 and SBA-15) in some other embodiments. The aforementioned porous dielectric materials are similar to diatomaceous earth, all are environmental friendly, toxin-free, and heat-stable and with high porosity and permeability and strong water absorption.

Referring to FIG. 1, the second electrode 40 which is porous allows perspiration to permeate to the sensing layer 30 and thus change the permittivity. Applying a bias voltage to the sensing layer 30 having the changed permittivity would generate a changed capacitance value of the capacitor-based fluid sensing unit 1. More particularly, the capacitance value before water absorption is $c=\varepsilon \times (A/d)$ and the capacitance value after water absorption is $\Delta c = \Delta \varepsilon \times (\Delta A/d)$. In these equations, $\varepsilon$ and $\Delta \varepsilon$ respectively denote the permittivity before and after water absorption; $A$ and $\Delta A$ respectively denote the diffusion areas before and after water absorption; and $d$ denotes the thickness of the sensing layer 30. In the present embodiments, the diffusion area $\Delta A$ is equal to the number of electrodes multiplied by the width W of the second electrode 40 and further multiplied by the length L of the second electrode 40. Table 1 provides the diffusion areas of electrodes with different lengths and widths when the numbers of electrodes are fixed to 5. As shown in Table 1, the diffusion area $\Delta A$ is 600,000 μm² if the number of electrodes is 5 and each electrode has a width W of 50 μm and a length L of 2400 μm; the diffusion area $\Delta A$ is 700,000 μm² if the number of electrodes is 5 and each electrode has a width W of 50 μm and a length L of 2800 μm. Some other combinations of width W and length L are also shown in Table 1. Accordingly, the present embodiments can be implemented in wearable devices and determining the perspiration volume with diffusion area and permittivity.

TABLE 1

| Number of electrodes | W(μm) | L(μm) | | A(μm²) | |
| --- | --- | --- | --- | --- | --- |
| 5 | 50 | 2400 | 2800 | 600,000 | 700,000 |
|  | 100 | 1200 | 1400 | 600,000 | 700,000 |
|  | 400 | 300 | 500 | 600,000 | 700,000 |

After the sensing layer 30 absorbed perspiration, the perspiration diffuses in the sensing layer 30 laterally and changes the permittivity of the sensing layer 30. The equations thus can be used to determine diffusion area on the premise that the thickness d of the sensing layer made of diatomaceous earth is known. The diffusion area is a variable affected by the perspiration volume in the embodiments, therefore the diffusion area can be used to determine the perspiration volume absorbed by the sensing layer 30. With a lower perspiration volume, the active sensing area of the second electrode 40 covered by the diffusion area ΔA with a width W is smaller and generates a lower capacitance value c. In contrast, with a higher perspiration volume, the active sensing area of the second electrode 40 covered by the diffusion area ΔA with a width W is larger and generates a higher capacitance value c. Accordingly, the perspiration volume can be determined with the diffusion area and the permittivity.

Figure 4:
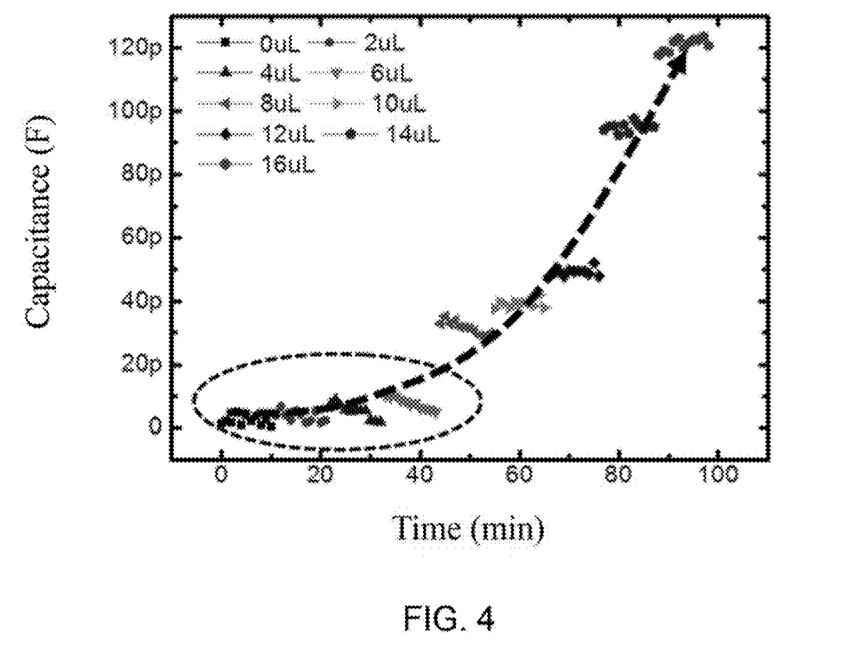
FIG. 4 is a chart illustrating the capacitance value detected under different volumes of a sample solution, in accordance with some embodiments of the present invention.
Figure 5:
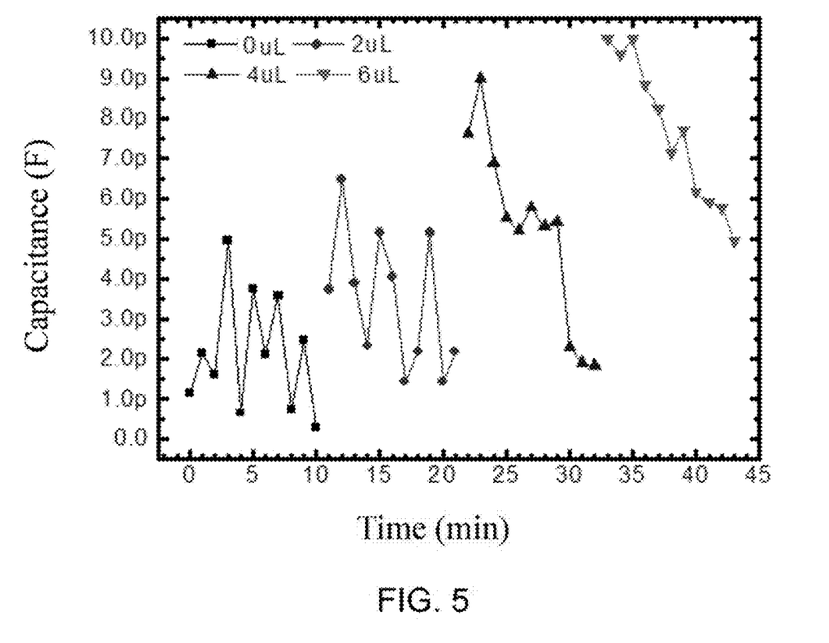
FIG. 5 is a chart illustrating the capacitance value detected under different volumes of a sample solution, in accordance with some embodiments of the present invention.

Referring to FIGS. 1, 4 and 5. FIG. 4 is a chart illustrating the capacitance value detected under different volumes of a sample solution in accordance with some embodiments of the present invention. Similarly, FIG. 5 is a chart illustrating the capacitance value detected under 0-6 μL of water in accordance with some embodiments of the present invention. In the embodiments, a capacitor-based fluid sensing unit 1 is provided. The capacitor-based fluid sensing unit 1 comprises a substrate 10 in PET, a first electrode 20 in gold disposed on the substrate 10, a sensing layer 30 in diatomaceous earth disposed on the first electrode 20, a second electrode 40 in gold disposed on the sensing layer 30. The sensing layer 30 in diatomaceous earth comprises silicon dioxide and little titanium dioxide and has a thickness of 1000 μm, and the second electrode 40 is a porous and comb-shaped electrode. With the porous electrodes and porous inorganic dielectric material, the permeability and water absorption are improved in the embodiments. The sensing layer was heated to 65° C. at a clearance step. After the clearance step, a solution (e.g., water of perspiration) was provided to the second electrode 40 and then permeated from the second electrode 40 to the sensing layer 30. In the next step, a first bias voltage was applied to the capacitor-based fluid sensing unit 1 and then detected the capacitance value of the capacitor-based fluid sensing unit to determining the volume of the solution. Finally, a second bias voltage was applied to the capacitor-based fluid sensing unit 1 to dry the sensing layer 30. The second bias voltage in the embodiments was to generate heat to dry the sensing layer 30. The sensing layer 30 can be reused after the water is evaporated. In some preferred embodiments, the step of applying the first bias voltage is performed 2 to 5 minutes after the step of providing the solution to the second electrode 40. In some preferred embodiments, the first bias voltage and the second bias voltage each is between 0.05 V and 0.1 V. In FIG. 4, the capacitor-based fluid sensing unit 1 was applied with a bias voltage at 0.5 V and repeated the method disclosed above to detect a solution in 0-16 μL sequentially. FIG. 5 is an enlarged chart from part of FIG. 4 encircled by the dashed line, comprising the results of 0-6 μL solution. The results in FIGS. 4 and 5 suggest that the detected capacitance value and the volume of solution are in proportion; the higher capacitance value is detected if more solution is provided.

Figure 6:
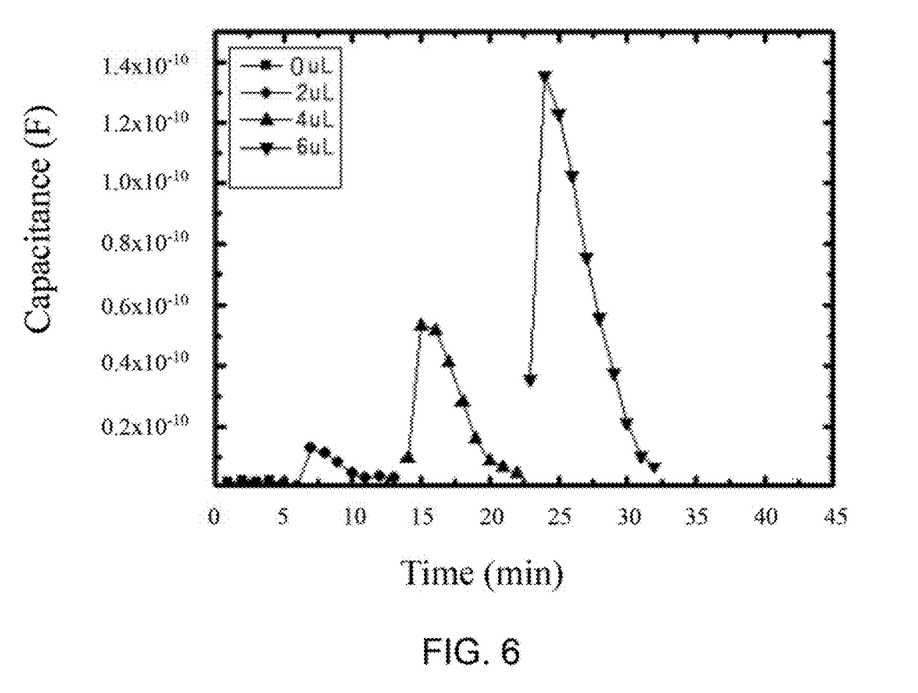
FIG. 6 is a chart illustrating the capacitance value detected under different volumes of a sample solution, in accordance with some embodiments of the present invention.
Figure 7:
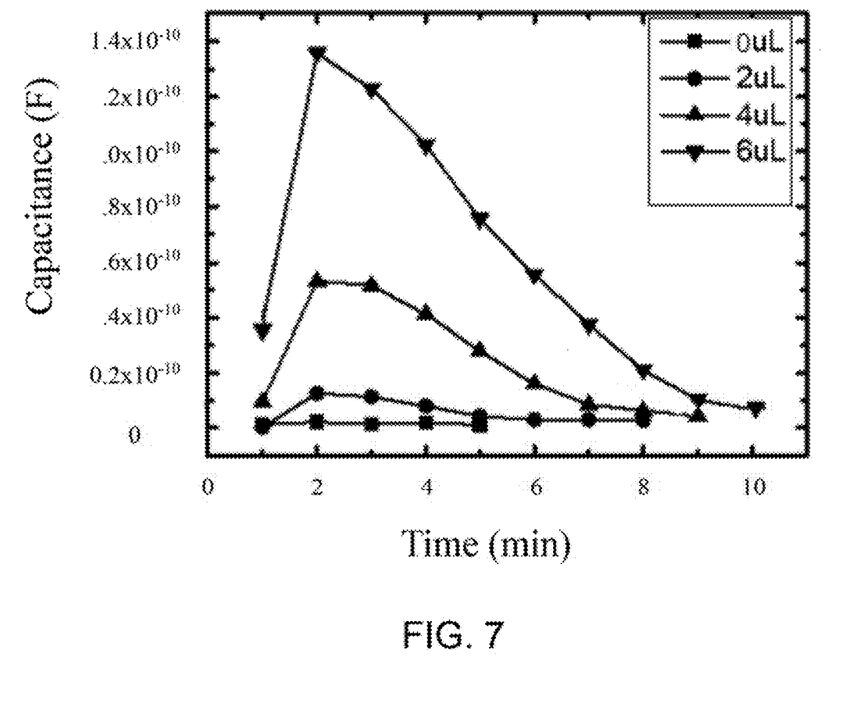
FIG. 7 is a chart illustrating the capacitance value detected under different volumes of a sample solution, in accordance with some embodiments of the present invention.

Referring to FIGS. 1, 6 and 7. FIG. 6 is a chart illustrating the capacitance value detected under different volumes of a sample solution in accordance with some embodiments of the present invention. FIG. 7 is a chart illustrating the capacitance value detected under different volumes of a sample solution, in accordance with some other embodiments of the present invention. In the embodiments, the capacitor-based fluid sensing unit comprises a substrate 10 in PET, a first electrode 20 in gold disposed on the substrate 10, a sensing layer 30 in filtered diatomaceous earth disposed on the first electrode 20, a second electrode 40 in gold disposed on the sensing layer 30. The sensing layer 30 in filtered diatomaceous earth comprises silicon dioxide and little titanium dioxide and has a thickness of 100 μm, and the second electrode 40 is a porous and comb-shaped electrode. With the porous electrodes and porous dielectric material, the permeability and water absorption are improved in the embodiments. After the sensing layer was heated to 65° C., a bias voltage at 0.5 V was applied to the capacitor-based fluid sensing unit 1 to detect 0-6 μL solution sequentially. As illustrated in FIG. 6, higher capacitance value was detected if more solution was provided. Accordingly, the detected capacitance value and the volume of solution are in proportion. FIG. 7 also illustrating a chart comprising results of 0-6 μL. Moreover, FIG. 7 suggests that the peak of detected capacitance value appeared at around 2 minutes after the solution was provided, no matter how much solution is introduced. Accordingly, the peak is not significantly affected by the volume of solution, therefore provides fast responses and stable results.

As indicated above, some embodiments of the present invention comprise porous electrodes and are toxin-free and environmental friendly. The porous and inorganic dielectric materials in the embodiments have the abilities to depose formaldehyde and total volatile organic compound (TOVC) and show superior efficiencies on permeability and water absorption. The capacitor-based fluid sensing units with such electrodes and dielectric materials provide fast response and sensitive results. The embodiments are suitable for being used in wearable devices to detect perspiration volume by sensing the permittivity and diffusion area. In addition, the embodiments continue to apply bias voltage to generate heat to dry the solution in the sensing layer. The capacitor-based fluid sensing unit can be reused after evaporation of the solution.

There are many inventions described and illustrated above. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

What is claimed is:

1. A capacitor-based fluid sensing unit, comprising:
   a substrate;
   a first electrode, disposed on the substrate;
   a sensing layer, disposed on the first electrode, wherein the sensing layer is made of a diatomaceous earth with silicon dioxide ($SiO_2$) and titanium dioxide ($TiO_2$), wherein the sensing layer has a thickness between 50 nm and 5 mm; and a second electrode, disposed on the sensing layer, wherein the second electrode with a length of 300-2800 μm, a width of 50-400 μm and a diffusion area is an interdigitated porous electrode, a comb-shaped porous electrode, or a mesh porous electrode;

wherein the capacitor-based fluid sensing unit detects a solution volume of 0-16 μL.

2. The capacitor-based fluid sensing unit as claimed in claim 1, wherein the first electrode and the second electrode each is made of one selected from the group consisting of gold (Au), silver (Ag), indium tin oxide (ITO), and the combination thereof.

3. The capacitor-based fluid sensing unit as claimed in claim 2, wherein the first electrode and the second electrode are made of gold.

4. The capacitor-based fluid sensing unit as claimed in claim 1, wherein the substrate is made of one selected from the group consisting of silicon wafer, glass, plastic, and the combination thereof.

5. The capacitor-based fluid sensing unit as claimed in claim 1, wherein the substrate is made of polyethylene terephthalate (PET).

6. An operating method of the capacitor-based fluid sensing unit as claimed in claim 1, comprising:

providing a solution to the second electrode;

applying a first bias voltage which is between 0.05 V and 0.1 V and is performed 2-5 minutes to the capacitor-based fluid sensing unit;

detecting a capacitance value of the capacitor-based fluid sensing unit;

determining a volume of the solution based on the capacitance value; and applying a second bias voltage which is between 0.05 V and 0.1 V to the capacitor-based fluid sensing unit to dry the sensing layer.

7. The method as claimed in claim 6, wherein the solution is water or perspiration.

8. A capacitor-based fluid sensing unit, comprising:

a substrate;

a first electrode, disposed on the substrate;

a sensing layer, disposed on the first electrode, wherein the sensing layer is made of a diatomaceous earth, wherein the sensing layer has a thickness between 50 nm and 5 mm; and a second electrode, disposed on the sensing layer, wherein the second electrode is an interdigitated porous electrode, a comb-shaped porous electrode, or a mesh porous electrode with a length of 300-2800 μm, a width of 50-400 μm and a diffusion area;

wherein the capacitor-based fluid sensing unit detects a solution volume of 0-16 μL.

* * * * *